United States Patent [19]
Bayrami

[11] Patent Number: 6,075,977
[45] Date of Patent: Jun. 13, 2000

[54] DUAL PURPOSE FLIP SHIELD FOR RETROFIT TO AN EXISTING HAND-HELD CELLULAR PHONE

[76] Inventor: Fred Bayrami, 76 Mariner's Dr., Southampton, N.Y. 11968

[21] Appl. No.: 08/950,022

[22] Filed: Oct. 14, 1997

[51] Int. Cl.[7] .................................................. H04B 1/38
[52] U.S. Cl. ............................. 455/90; 455/128; 343/841
[58] Field of Search ............................. 455/90, 575, 128; 343/702, 841

[56] References Cited

U.S. PATENT DOCUMENTS

| | | | |
|---|---|---|---|
| 5,338,896 | 8/1994 | Danforth | 174/35 |
| 5,444,866 | 8/1995 | Cykiert | 455/89 |
| 5,507,012 | 4/1996 | Luxon | 455/89 |
| 5,613,221 | 3/1997 | Hunt | 455/89 |
| 5,678,206 | 10/1997 | Ishii | 455/90 |
| 5,694,137 | 12/1997 | Wood | 343/702 |
| 5,819,162 | 10/1998 | Spann | 455/90 |
| 5,826,201 | 10/1998 | Gratias | 455/575 |

*Primary Examiner*—Daniel S. Hunter
*Assistant Examiner*—Nick Corsaro

[57] ABSTRACT

A shield for an existing hand-held telephone having a front face with at least a display and a keypad thereon, and an antenna for emitting electromagnetic waves. The shield includes a body portion and apparatus for pivotally mounting the body portion to the existing hand-held cellular telephone. The body portion is pivotally mounted to the existing hand-held cellular telephone and has a first position for covering and protecting the front face of the existing hand-held cellular telephone, and a second position that is substantially 180° pivoted upwardly from the first position and is disposed adjacent to, and between, the antenna of the existing hand-held cellular telephone and a user and extends at least the length of the antenna of the existing hand-held cellular telephone so as the electromagnetic waves are emitted from the antenna of the existing hand-held cellular telephone, the body portion shields the user from them. When in the second position, the body portion has a polished convex face that opposes the antenna of the existing hand-held cellular telephone so as to reflect the electromagnetic waves emitted from the antenna of the existing hand-held cellular telephone at diffusing angles and cause them to spread out and reflect off nearby surfaces and provide a more non-uniformity in the transmission direction so as to improve communications of the existing hand-held cellular telephone.

7 Claims, 2 Drawing Sheets

DUAL PURPOSE FLIP SHIELD FOR RETRO-FIT TO AN EXISTING HAND-HELD CELLULAR PHONE

BACKGROUND OF THE INVENTION

1. Field of the Invention

The present invention relates to a shield. More particularly, the present invention relates to a dual purpose flip shield for retro-fitting to an existing hand-held cellular telephone.

2. Description of the Prior Art

Numerous innovations for shields for cellular telephones have been provided in the prior art that will be described. Even though these innovations may be suitable for the specific individual purposes to which they address, however, they differ from the present invention, and will be described infra chronology to illustrate the alleged advancement of the art.

FOR EXAMPLE, U.S. Pat. No. 5,335,366 to Daniels teaches a radiation shielding apparatus for a radio transmitting device, such as a cellular phone. A radiation shield is disposed between a radiation component and a user to prevent unwanted exposure of the user to emanating radiation from the radiation emanating component. The cellular telephone radio transmitting device may be a hand-held cellular telephone, and the radiation emanating component may be an internal or external antennas or any other electromagnetic radiation source, such as a transmitter. The radiation shield can be retrofitted to an existing cellular telephone, or may be designed specific for different models of cellular phones. The radio shield can absorb, block, and/or reflect electromagnetic wave radiation to shield the user of such cellular telephones from unwanted and possibly harmful exposure to electromagnetic wave radiation.

ANOTHER EXAMPLE, U.S. Pat. No. 5,338,896 to Danforth teaches a shield device for any phone with an antenna that emits and receives microwaves, in particular cellular phones. The shield device protects a user by blocking the passage of microwaves to and from the cellular phone antenna while the phone is in use. In the first embodiment of the invention, the shield device comprises a rectangular shaped body with an upper tab for attaching the shield device to the antenna and two opposing lower tabs for attaching the shield device to the upper portion of the cellular phone. The shield device consists of a cover with a pocket for receiving the shielding member. In a second embodiment of the invention, the shield device contemplates a semi-circular hollow tubular member adapted to fit over an antenna. The tubular member has an elastic bottom portion adapted to fit firmly over the antenna ferrule. The bottom portion of the tubular member consists of a resilient disk member, thus protecting the user from any microwaves emitted and received by the antenna. In a third embodiment of the invention, the shield device comprises a hollow tubular member with telescoping members of a collapsible, retractable form.

STILL ANOTHER EXAMPLE, U.S. Pat. No. 5,367,309 to Tashjian teaches a shielding device used on hand-held cellular phones that comprises a substantially rectangular shield which extends adjacent to the antenna. A downwardly extending slide arm portion of the shield terminates in a substantially pointed end surface formed by the outer edge of the shield sloping inwardly to engage the inner edge of the slide arm, with the outer edge having a notch on the exterior surface thereof. The device also includes a paddle arm portion extending perpendicular to the shield area and then downwardly to terminate in an enlarged paddle engaging the rear of the phone. The shield is mounted to a hand-held cellular phone with the shield area extending vertically upwardly adjacent to the antenna and the paddle arm extending over the top of the phone and terminating in the rear paddle. The shield is held in place by an O-ring which surrounds the phone and fits in the notch in the slide arm. The shield comprises polished aluminum while the slide arm and paddle arms are coated with plastic vinyl to enhance friction and prevent scratching of the phone surface. The shielding area deflects a majority of the radiation and simultaneously absorbs whatever is not deflected while physically blocking the user from actual contact with the antenna when in use.

YET ANOTHER EXAMPLE, U.S. Pat. No. 5,444,866 to Cykiert teaches a device for shielding a user from electromagnetic waves emitted from a cellular telephone. The device includes a shielding member extending between the antenna of the telephone and a user and configured to encompass the antenna on three sides.

FINALLY, STILL YET ANOTHER EXAMPLE, U.S. Pat. No. 5,613,221 to Hunt teaches a radiation shield for a hand-held telephone made up of a metal strip placed between the antenna rod of the telephone and the speaker. The strip has a flat body portion and an upper portion that is curved away from the rod. Overall length of the strip is slightly longer than the antenna rod, and its width is 1 to 1.5 inches. Radiation fields reaching the head of a user whose ear is placed near the speaker are substantially reduced by the shield.

It is apparent that numerous innovations for shields for cellular telephones have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

ACCORDINGLY, AN OBJECT of the present invention is to provide a dual purpose flip shield for retrofitting to an existing hand-held cellular telephone that avoids the disadvantages of the prior art.

ANOTHER OBJECT of the present invention is to provide a dual purpose flip shield for retrofitting to an existing hand-held cellular telephone that is simple and inexpensive to manufacture.

STILL ANOTHER OBJECT of the present invention is to provide a dual purpose flip shield for retrofitting to an existing hand-held cellular telephone that is simple to use.

BRIEFLY STATED, YET ANOTHER OBJECT of the present invention is to provide a shield for an existing hand-held telephone having a front face with at least a display and a keypad thereon, and an antenna for emitting electromagnetic waves. The shield includes a body portion and apparatus for pivotally mounting the body portion to the existing hand-held cellular telephone. The body portion is pivotally mounted to the existing hand-held cellular telephone and has a first position for covering and protecting the front face of the existing hand-held cellular telephone so as to prevent damage to at least the display and the unintentional use of the keypad, and a second position that is substantially 180° pivoted upwardly from the first position and is disposed adjacent to, and between, the antenna of the existing hand-held cellular telephone and a user and extends at least the length of the antenna of the existing hand-held cellular telephone so as the electromagnetic waves are emitted from the antenna of the existing hand-held cellular telephone, the body portion shields the user from them. When in the second position, the body portion has a polished convex face that opposes the antenna of the existing hand-held cellular telephone so as to reflect the electromagnetic waves emitted from the antenna of the existing hand-held cellular telephone at diffusing angles and cause them to spread out and reflect off nearby surfaces and provide a more non-uniformity in the transmission direction so as to improve communications of the existing hand-held cellular telephone.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures of the drawing are briefly described as follows.

Figure 1:
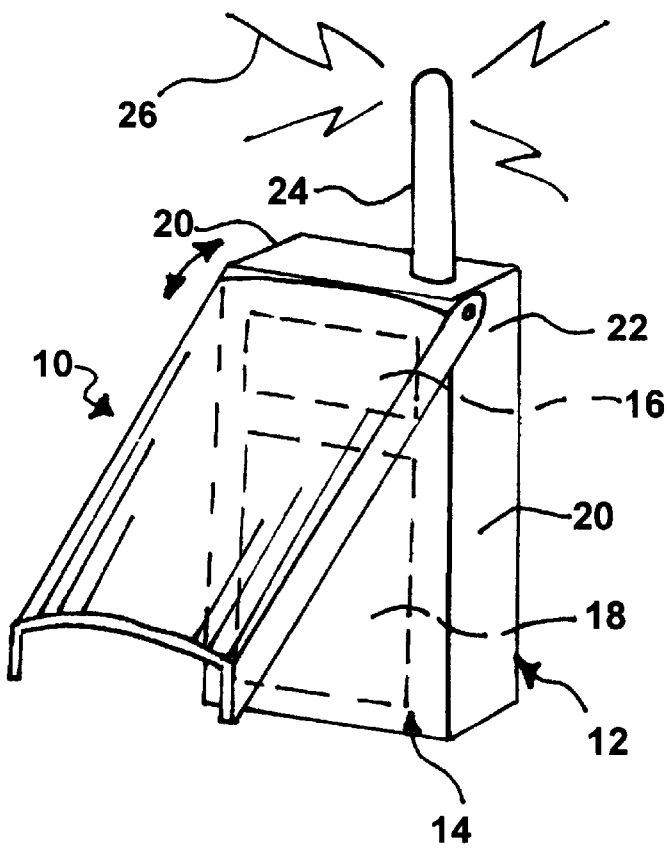
FIG. 1 is a diagrammatic perspective view of the present invention retrofitted to an existing hand-held cellular telephone.

LIST OF REFERENCE NUMERALS UTILIZED IN THE DRAWING 10 dual purpose flip shield for retrofitting to an existing hand-held cellular telephone of the present invention 12 existing hand-held telephone 14 front face of existing hand-held telephone 12

16 display on front face 14 of existing hand-held telephone 12

18 keypad on front face 14 of existing hand-held telephone 12

20 pair of opposing side walls of existing hand-held telephone 12

22 upper portion of existing hand-held telephone 12

24 antenna extending from upper portion 22 of existing hand-held telephone 12

26 electromagnetic waves emitted from antenna 24 extending from upper portion 22 of existing hand-held telephone 12

28 body portion 30 first position of body portion 28

32 second position of body portion 28

34 user 36 apparatus for pivotally mounting body portion 28 to existing hand-held cellular telephone 12

38 portion of body portion 28

39 long edges of facia portion 38 of body portion 28

40 concave face of facia portion 38 of body portion 28

42 convex face of facia portion 38 of body portion 28

44 pair of opposing side walls of body portion 28

46 pair of tabs of pair of opposing side walls 44 of body portion 28 of apparatus 36

48 throughbore in each tab of pair of tabs 46 of pair of opposing side walls 44 of body portion 28 of apparatus 36

49 space formed between pair of tabs 46 of pair of opposing side walls 44 of body portion 28 of apparatus 36

50 pair of feet of apparatus 36

52 countersunk throughbore in each foot of pair of feet 50 of apparatus 36

54 pair of pivot rivets of apparatus 36

56 head of each pivot rivet of pair of pivot rivets 54 of apparatus 36

58 adhesive coated on pair of feet 50 and heads 56 of pair of pivot rivets 54 of apparatus 36

DETAILED DESCRIPTION OF THE PREFERRED EMBODIMENT

Referring now to the figures in which like numerals indicate like parts, and particularly to FIG. 1, the dual purpose flip shield for retrofitting to an existing hand-held cellular telephone of the present invention is shown generally at 10 retro-fitted to an existing hand-held telephone 12 having a front face 14 with at least a display 16 and a keypad 18 thereon, a pair of opposing side walls 20, and an upper portion 22 with an antenna 24 having a length extending upwardly therefrom for emitting electromagnetic waves 26.

The configuration of the dual purpose flip shield for retro-fitting to an existing hand-held cellular telephone 10 can best be seen in FIG. 2 and FIG. 3, and as such will be discussed with reference thereto.

Figure 2:
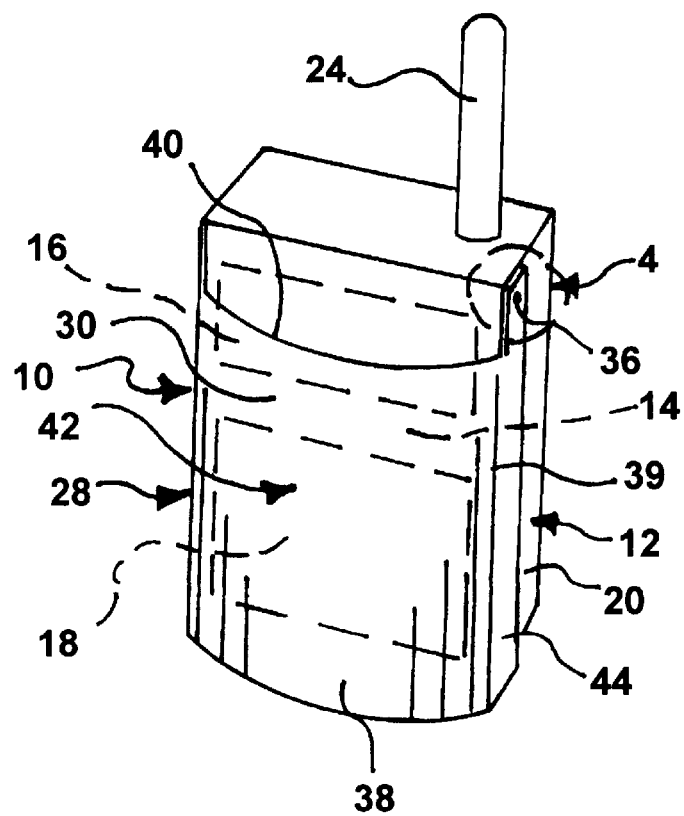
FIG. 2 is a diagrammatic perspective view of the present invention in a first position covering and protecting the front face of the existing hand-held cellular telephone.

As shown in FIG. 2, the dual purpose flip shield for retro-fitting to an existing hand-held cellular telephone 10 comprises a body portion 28 for pivotal mounting to the existing hand-held cellular telephone 12, and has a first position 30 for covering and protecting the front face 14 of the existing hand-held cellular telephone 12 so as to prevent damage to at least the display 16 and the unintentional use of the keypad 18.

Figure 3:
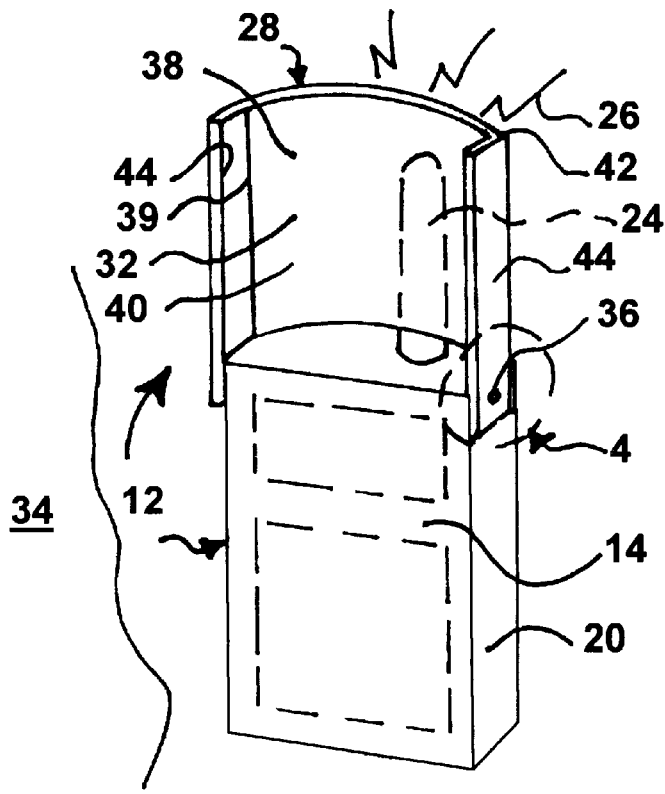
FIG. 3 is a diagrammatic perspective view of the present invention in a second position shielding a user from the electromagnetic waves emanating from the antenna of the existing hand-held cellular telephone.

As shown in FIG. 3, the body portion 28 further has a second position 32 that is substantially 180° pivoted upwardly from the first position 30 for being disposed adjacent to, and between, the antenna 24 of the existing hand-held cellular telephone 12 and a user 34 and for extending at least the length of the antenna 24 of the existing hand-held cellular telephone 12 so as the electromagnetic waves 26 are emitted from the antenna 24 of the existing hand-held cellular telephone 12, the body portion 28 shields the user 34 from them.

As shown in FIG. 2 and FIG. 3, the dual purpose flip shield for retrofitting to an existing hand-held cellular telephone 10 further comprises apparatus 36 for pivotally mounting the body portion 28 to the existing hand-held cellular telephone 12.

The configuration of the body portion 28 can best be seen in FIG. 2 and FIG. 3, and as such will be discussed with reference thereto.

The body portion 28 is rectangular-shaped in front and rear views and convexo-concave-shaped in lateral profile, and comprises a facia portion 38 that has a concave face 40 for extending over, and opposing, the front face 14 of the existing hand-held cellular telephone 12 when the body portion 28 is in the first position 30 and a convex face 42 for extending the length of, and opposing, the antenna 24 of the existing hand-held cellular telephone 12 when the body portion 28 is in the second position 32.

The convex face 42 of the facia portion 38 of the body portion 28 is a polished material, preferably aluminum, so as to provide high reflectance of the electromagnetic waves 26 away from the user 34, and is one of parabolic and hyperbolic so as to reflect the electromagnetic waves 26 emitted from the antenna 24 of the existing hand-held cellular telephone 12 at diffusing angles and cause them to spread out and reflect off nearby surfaces and provide a more non-uniformity in the transmission direction so as to improve communications of the existing hand-held cellular telephone 12.

The body portion 28 further comprises a pair of opposing side walls 44 depending from the facia portion 38, at its long edges 39, and for opposing the pair of opposing side walls 20 of the existing hand-held cellular telephone 12 when the body portion 28 is in the first position 30.

Figure 4:
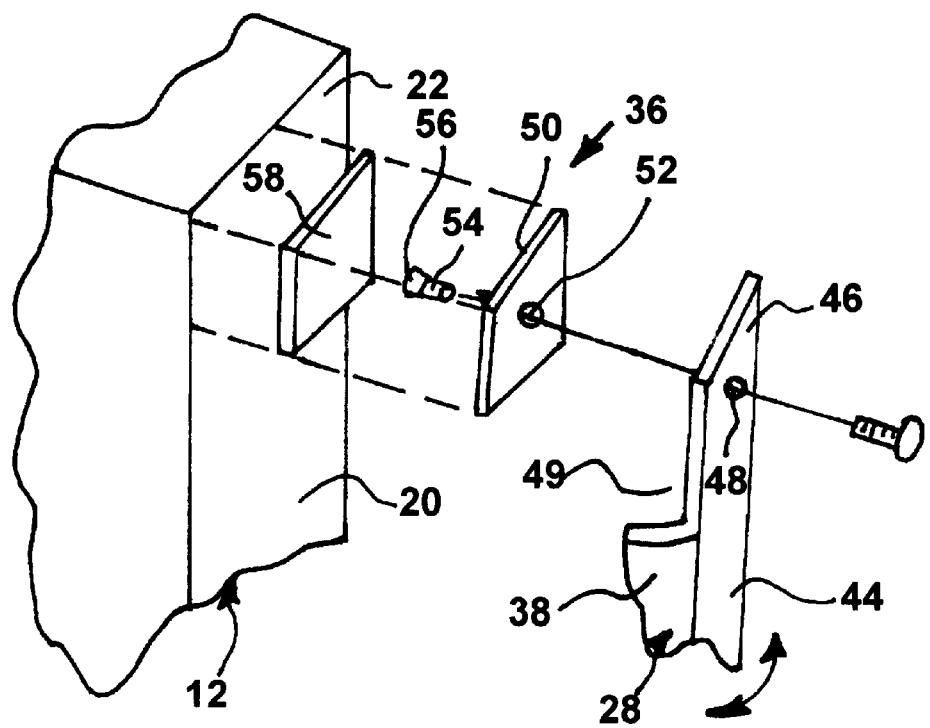
FIG. 4 is an exploded diagrammatic perspective view of the area generally enclosed by the dotted ellipse identified by ARROW 4 in FIG. 2 and FIG. 3, illustrating the apparatus for pivotally mounting the present invention to the existing hand-held cellular telephone.

The configuration of the apparatus 36 can best be seen in FIG. 4, and as such will be discussed with reference thereto.

The apparatus 36 comprises the pair of opposing side walls 44 of the body portion 28 having a pair of tabs 46, each of which has a throughbore 48 therethrough. Each tab of the pair of tabs 46 extends longitudinally and coplanarly from a respective side wall of the pair of opposing side walls 44 of the body portion 28 for pivotal mounting to a respective side wall of the pair of opposing side walls 20 of the existing hand-held cellular telephone 12, at the upper portion 22 thereof so as the body portion 28 pivots between the first and second positions 30, 32, a space 49 formed between the pair of tabs 46 provides clearance for the facia portion 38 of the body portion 28.

The apparatus 36 further comprises a pair of feet 50, each of which has a countersunk throughbore 52 therethrough and is for affixing to the respective side wall of the pair of opposing side walls 20 of the existing hand-held cellular telephone 12, at the upper portion 22 thereof.

The apparatus 36 further comprises a pair of pivot rivets 54, each of which extends laterally outwardly through the countersunk throughbore 52 in a respective foot of the pair of feet 50, with its head 56 resting in the countersunk so as to prevent its interference with the respective side wall of the pair of opposing side walls 20 of the existing hand-held cellular telephone 12, and through the throughbore 48 in a respective tab of the pair of the tab 46, where it is flattened.

The pair of feet 50 and the head 56 of each pivot rivet of the pair of pivot rivets 54 are coated with an adhesive 58 so as to allow the pair of pivot rivets 54 to be fixed when the pair of feet 50 are affixed to the pair of opposing side walls 20 of the existing hand-held cellular telephone 12 and have the body portion 28 pivot relative thereto.

It will be understood that each of the elements described above, or two or more together, may also find a useful application in other types of constructions differing from the types described above.

While the invention has been illustrated and described as embodied in a dual purpose flip shield for retrofitting to an existing hand-held cellular telephone, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

What is claimed is:

1. A shield for an existing hand-held telephone having a front face with at least a display and a keypad thereon, a pair of opposing side walls, and an upper portion with an antenna having a length extending upwardly therefrom for emitting electromagnetic waves, said shield comprising:

a) a body portion for pivotal mounting to the existing hand-held cellular telephone and having a first position for covering and protecting the front face of the existing hand-held cellular telephone so as to prevent damage to at least the display and the unintentional use of the keypad, and a second position being substantially 180° pivoted upwardly from said first position for being disposed adjacent to, and between, the antenna of the existing hand-held cellular telephone and a user and for extending at least the length of the antenna of the existing hand-held cellular telephone so as the electromagnetic waves are emitted from the antenna of the existing hand-held cellular telephone, said body portion shields the user from them; said body portion comprising a facia portion having a concave face for extending over, and opposing, the front face of the existing hand-held cellular telephone when said body portion is in said first position and a convex face for extending the length of, and opposing, the antenna of the existing hand-held cellular telephone when said body portion is in said second position; said body portion further comprising a pair of opposing side walls depending from said facia portion, at its long edges, and for opposing the pair of opposing side walls of the existing hand-held cellular telephone when said body portion is in said first position; and b) means for pivotally mounting said body portion to the existing hand-held cellular telephone; said means including said pair of opposing side walls of said body portion having a pair of tabs, each of which having a throughbore therethrough; each tab of said pair of tabs extending longitudinally and coplanarly from a respective side wall of said pair of opposing side walls of said body portion for pivotal mounting to a respective side wall of the pair of opposing side walls of the existing hand-held cellular telephone, at the upper portion thereof, so as said body portion pivots between said first and second positions, a space formed between said pair of tabs provides clearance for said facia portion of said body portion; said means further including a pair of feet, each of which having a countersunk throughbore therethrough and being for affixing to the respective side wall of the pair of opposing side walls of the existing hand-held cellular telephone, at the upper portion thereof.

2. The shield as defined in claim 1, wherein said body portion is rectangular-shaped in front and rear views and convexo-concave-shaped in lateral profile.

3. The shield as defined in claim 1, wherein said convex face of said facia portion of said body portion is a polished material so as to reflect the electromagnetic waves away from the user.

4. The shield as defined in claim 3, wherein said polished material is aluminum so as to provide high reflectance.

5. The shield as defined in claim 1, wherein said convex face of said body portion is one of parabolic and hyperbolic so as to the electromagnetic waves emitted from the antenna of the existing hand-held cellular telephone at diffusing angles and cause them to spread out and reflect off nearby surfaces and provide a more non-uniformity in the transmission direction so as to improve communications of the existing hand-held cellular telephone.

6. The shield as defined in claim 1, wherein said means further includes a pair of pivot rivets, each of which extends laterally outwardly through said countersunk throughbore in a respective foot of said pair of feet, with its head resting in the countersunk so as to prevent its interference with the respective side wall of the pair of opposing side walls of the existing hand-held cellular telephone, and through said throughbore in a respective tab of said pair of tabs, where it is flattened.

7. The shield as defined in claim 6, wherein said pair of feet and said head of each pivot rivet of said pair of pivot rivets are coated with an adhesive so as to allow said pair of pivot rivets to be fixed when said pair of feet are affixed to the pair of opposing side walls of the existing hand-held cellular telephone, and have said body portion pivot relative thereto.

* * * * *